United States Patent [19]

Mayer et al.

[11] Patent Number: 4,908,447
[45] Date of Patent: Mar. 13, 1990

[54] 2-,6-DIPHENYLPYRIDINE COMPOUNDS USEFUL AS DYE PRECURSORS

[75] Inventors: Udo Mayer, Frankenthal; Friedrich-Wilhelm Raulfs, Ludwigshafen, both of Fed. Rep. of Germany

[73] Assignee: BASF Aktiengesellschaft, Ludwigshafen, Fed. Rep. of Germany

[21] Appl. No.: 298,267

[22] Filed: Jan. 17, 1989

Related U.S. Application Data

[63] Continuation of Ser. No. 97,167, Sep. 16, 1987, abandoned.

[30] Foreign Application Priority Data

Sep. 20, 1986 [DE] Fed. Rep. of Germany ....... 3632009

[51] Int. Cl.$^4$ .................. C07D 401/02; C07D 213/38
[52] U.S. Cl. .................................... 544/124; 544/360; 546/194; 546/272; 546/275; 546/329; 546/330
[58] Field of Search ............... 546/194, 272, 275, 329, 546/330; 544/124, 360

[56] References Cited

U.S. PATENT DOCUMENTS 4,262,078 4/1981 Ishida et al. ..................... 430/109
4,363,503 12/1982 Schmidt et al. ................... 546/329

Primary Examiner—Mary C. Lee
Assistant Examiner—Zinna Northington-Davis
Attorney, Agent, or Firm—Oblon, Spivak, McClelland, Maier & Neustadt

[57] ABSTRACT

Pyridine compounds of the general formula

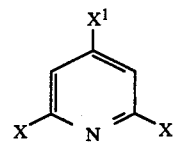

where one radical X is phenyl and the other radical X is phenyl which is substituted by halogen, cyano, $C_1$–$C_5$-alkyl, $C_1$–$C_5$-alkoxy or $C_1$–$C_5$-alkoxycarbonyl, or both radicals X are 4-fluorophenyl, and $X^1$ is a radical of the formula

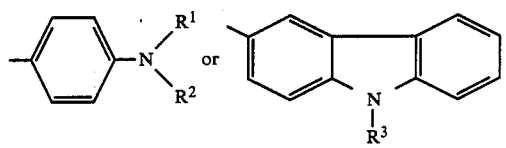

where $R^1$ and $R^2$ independently of one another are each straight-chain or branched alkyl, cyanoalkyl, haloalkyl, aryl or aralkyl having a total of 7 to 14 carbon atoms, or

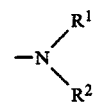

is a 5-membered or 6-membered saturated heterocyclic radical and $R^3$ is straight-chain or branched $C_1$–$C_4$-alkyl, are described.

The compounds (I) are dye precursors for pressure-sensitive recording systems.

9 Claims, No Drawings

2-,6-DIPHENYLPYRIDINE COMPOUNDS USEFUL AS DYE PRECURSORS

This application is a continuation of application Ser. No. 07/097,167, filed on Sept. 16, 1987, now abandoned.

DE-A 2 227 597 discloses symmetrical pyridine compounds which contain phenyl and p-methoxyphenyl radicals in the 2- and 6-position.

GB-A 2 029 591 discloses a dye precursor which contains 4-chlorophenyl in the 2- and 6-position, for use in a photographic copying process.

Amino-substituted phenyl rings at the 2- and 6-position of the pyridine ring are disclosed in EP-A-061 128.

These dye precursors are suitable for pressure-sensitive recording systems but have disadvantages in use, for example insufficient solubility, excessive migration and excessive coloring of coating paper.

It is an object of the present invention to provide dye precursors which have improved properties with respect to solubility, migration and coloring of coating paper.

We have found that this object is achieved by pyridine compounds of the general formula (I)

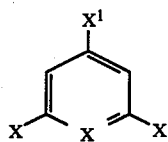

(I)

where one radical X is phenyl and the other radical X is phenyl which is monosubstituted or disubstituted by halogen, cyano, $C_1$–$C_5$-alkyl, $C_1$–$C_5$-alkoxy or $C_1$–$C_5$-alkoxycarbonyl, or both radicals X are 4-fluorophenyl, and $X^1$ is a radical of the formula

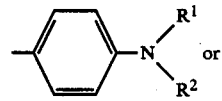

(II)

or

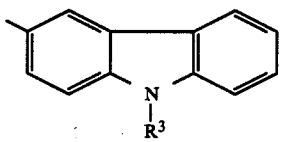

(III)

where $R^1$ and $R^2$ independently of one another are each straight-chain or branched $C_1$–$C_8$-alkyl, cyano-$C_2$–$C_5$-alkyl, halo-$C_1$–$C_5$-alkyl, aryl or aralkyl having a total of 7 to 14 carbon atoms, or

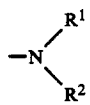

is a 5-membered or 6-membered saturated heterocyclic radical and $R^3$ is straight-chain or branched $C_1$–$C_4$-alkyl.

The pyridine compounds are pale yellow or colorless. They dissolve in glacial acetic acid to give yellow to orange solutions. In neutral or basic organic solvents, colorless solutions are obtained. Color formation can also be effected by means of kaolin, zeolites, bentonite, silica, alum, zinc sulfate, oxalic acid and phenolic condensates. Because of this property, the compounds are suitable for use as dye precursors for pressure-sensitive recording material, in particular for the production of copying papers.

Compared with the prior art pyridine derivatives which give yellow to orange colorations, the pyridine compounds (I) exhibit less migration. The compounds (I) furthermore color coating paper to a lesser extent, both at room temperature and at 150° C. Some pyridine compounds (I) have better solubility in the media used than do the prior art pyridine derivatives.

One radical X is phenyl and the other radical X is phenyl which is substituted by halogen, cyano, $C_1$–$C_5$-alkyl, $C_1$–$C_5$-alkoxy or $C_1$–$C_5$-alkoxycarbonyl, or both radicals X are 4-fluorophenyl. Halogen is bromine or, preferably, chlorine or fluorine. The number of substituents on this radical X is one or two, preferably one, in the case of chlorine one or two.

Specific examples of the other radical X are 3- and 4-methylphenyl, 2- and 4-methoxyphenyl, 4-chlorophenyl, 4-bromophenyl, 4-fluorophenyl, 2-carboethoxyphenyl, 4-cyanophenyl and 3,4-dichlorophenyl, of which 4-fluorophenyl and in particular 4-chlorophenyl are preferred.

$X^1$ is a radical of the formula (II) or (III). In (II), $R^1$ and $R^2$ independently of one another are each straight-chain, branched or cyclic $C_1$–$C_8$-alkyl, such as methyl, ethyl, propyl, isopropyl, butyl, isobutyl, tert-butyl, hexyl, cyclohexyl, 2-ethylhexyl or octyl, cyano-$C_2$–$C_5$-alkyl, such as 2-cyanoethyl, or halo-$C_1$–$C_5$-alkyl, such as 2-chloroethyl, 2-bromoethyl, 2-chloropropyl, 3-bromopropyl or 4-chlorobutyl.

Aryl is preferably unsubstituted or substituted phenyl, and aralkyl is phenalkyl having a total of 7 to 14 carbon atoms, eg. p-xylyl, m-xylyl, o-xylyl, cumyl, 1-phenylhexyl, benzyl or 2-phenylethyl.

$R^1$ and $R^2$ are each preferably methyl, ethyl, butyl, 2-cyanoethyl, 2-chloroethyl or benzyl.

may furthermore be the radical of a 5-membered or 6-membered saturated heterocyclic ring, eg. piperidinyl, morpholinyl, piperazinyl, pyrrolidinyl or N'-$C_1$–$C_4$-alkylpiperazinyl. In (III), $R^3$ is $C_1$–$C_4$-alkyl, preferably methyl or ethyl.

$X^1$ is preferably 4-N-benzyl-N-ethylaminophenyl, 4-N-(2'-cyanoethyl)-N-butylaminophenyl, 4-N-(2'-cyanoethyl)-N-methylaminophenyl or, in particular, 4-N,N-dimethylaminophenyl.

The pyridine compounds (I) are obtained, for example, by reacting a vinylketone of the formula (IV)

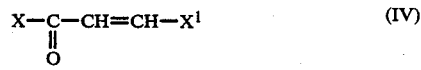

(IV)

with a quaternary ammonium salt of the general formula (V)

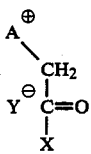
(V)

in the presence of ammonia or an ammonia-donating agent in acetic acid.

In formula (V), A is either an ammonium group of the formula (VI)

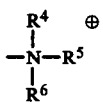
(VI)

where $R^4$, $R^5$ and $R^6$ independently of one another are each straight-chain or branched $C_1$–$C_8$-alkyl, and $R^4$ and $R^5$ together with the N atom of the ammonium group may furthermore be a saturated 5-membered or 6-membered heterocyclic ring, or a pyridinium radical of the formula (VII)

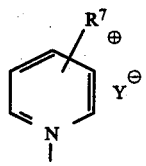
(VII)

where $R^7$ is hydrogen or straight-chain or branched $C_1$–$C_4$-alkyl and $Y^-$ is an organic or inorganic anion, preferably chloride or bromide.

The Examples which follow illustrate the invention.

In the Examples, parts and percentages are by weight.

EXAMPLE 1

10.06 parts of 1-(4'-fluorophenacyl)-pyridinium chloride and 10.76 parts of 1-(4-fluorophenyl)-3-(4'-dimethylaminophenyl)-1-oxoprop-2-ene are heated at 130° C. for 8½ hours together with 34 parts of ammonium acetate in 50 parts of glacial acetic acid. The mixture is stirred for 17 hours at room temperature, after which the precipitated colorless crystals are filtered off under suction, washed with methanol and water and dried at 60° C. in a drying oven to give 10.5 parts of 4-(4-dimethylamino-phenyl)-2,6-bis-(4'-fluorophenyl)-pyridine, which dissolves in glacial acetic acid to give an orange yellow coloration (λmax: 431 nm).

EXAMPLE 2

The method used is the same as that described in Example 1, except that, instead of 10.06 parts of 1-(4-fluorophenacyl)-pyridinium chloride, 10.94 parts of (4-fluorophenacyl)-triethylammonium chloride are used. The yield after heating for 13 hours at 120° C. is 2.3 parts of 4-(4-dimethylaminophenyl)-2,6-bis-(4-fluorophenyl)-pyridine.

EXAMPLE 3

13.9 parts of 1-phenacylpyridinium bromide and 14.27 parts of 1-(4-chlorophenyl)-3-(4-dimethylaminophenyl)-1-oxoprop-2-ene are heated at 120° C. for 3.5 hours together with 34 parts of ammonium acetate in 50 parts of glacial acetic acid. Working up as described in Example 1 gives 4-(4'-dimethylaminophenyl)-2-(4'-chlorophenyl)-6-phenylpyridine in the form of a colorless powder, which dissolves in glacial acetic acid to give a yellow color (λmax: 425 nm).

EXAMPLES 4 TO 15

The following pyridine compounds (I) are prepared similarly to Examples 1 to 3:

| Example | $X^2$ | $X^1$ | $X^3$ | λ max [nm] |
|---|---|---|---|---|
| 4 | Phenyl | 4-Dimethylaminophenyl | 2-Methoxyphenyl | 436 |
| 5 | Phenyl | 4-Dimethylaminophenyl | 4-Methylphenyl | 425 |
| 6 | Phenyl | 4-Dimethylaminophenyl | 3-Methylphenyl | 430 |
| 7 | Phenyl | 4-Dimethylaminophenyl | 4-Fluorophenyl | 425 |
| 8 | Phenyl | 4-(2-Cyanoethyl)-methylaminophenyl | 4-Chlorophenyl | 425 |
| 9 | Phenyl | 4-Butyl-(2-cyanoethyl)-aminophenyl | 4-Chlorophenyl | 428 |
| 10 | Phenyl | 9-Ethylcarbazol-3-yl | 4-Chlorophenyl | 407 |
| 11 | Phenyl | 4-Benzylethylaminophenyl | 4-Chlorophenyl | 439 |
| 12 | Phenyl | 4-(2-Chloroethyl)-ethylaminophenyl | 4-Chlorophenyl | 436 |
| 13 | Phenyl | 4-Dimethylaminophenyl | 2-Carboethoxyphenyl | 433 |
| 14 | Phenyl | 4-Dimethylaminophenyl | 4-Cyanophenyl | 444 |
| 15 | Phenyl | 4-Dimethylaminophenyl | 3,4-Dichlorophenyl | 442 |

EXAMPLE 16

9.9 parts of 3-methyl-1-phenacylpyridinium chloride, 11.4 parts of 1-(4-chlorophenyl)-3-(4-dimethylaminophenyl)-1-oxoprop-2-ene and 34 parts of ammonium chloride in 50 parts of glacial acetic acid are refluxed for 2.5 hours. White crystals of 2-(4'-chlorophenyl)-4-(4'-dimethylaminophenyl)-6-phenylpyridine are precipitated from the red solution after one hour. The mixture is stirred for 17 hours at room temperature, after which the crystals are filtered off under suction, washed with methanol and water and dried at 60° C. The yield is 12 parts of a product which is identical to that obtained in Example 3.

We claim:

1. A pyridine compound of the formula:

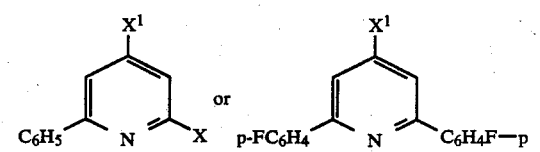

wherein radial X is phenyl which is monosubstituted or disubstituted by halogen, cyano, $C_1$–$C_5$-alkyl, $C_1$–$C_5$-alkoxy or $C_1$–$C_5$-alkoxycarbonyl and $X^1$ is a radical of the formula:

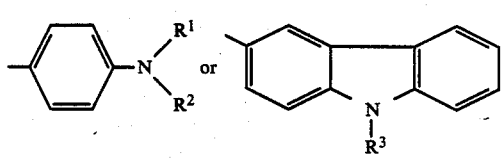

wherein $R^1$ and $R^2$ independently of one another are each straight-chain or branched $C_1$–$C_8$-alkyl, cyano- C2–C5-alkyl, halo-C1–C5-alkyl, phenyl or phenalkyl having a total of 7 to 14 carbon atoms, or

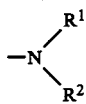

is a radical selected from the group consisting of N-piperidinyl, N-morpholinyl, N-piperazinyl, pyrrolidinyl and N'-C1–C4-alkylpiperazinyl, and $R^3$ is straight-chain or branched C1–C4-alkyl.

2. The pyridine compound as claimed in claim 1, wherein radical X is 4-fluorophenyl, 4-chlorophenyl, 4-methylphenyl, 4-methoxyphenyl, 2-methoxyphenyl, 2-carboethoxyphenyl, 4-cyanophenyl or 3,4-dichlorophenyl.

3. The pyridine compound as claimed in claim 1, wherein $X^1$ is 4-N,N-dimethylaminophenyl, 4-N-(2'-cyanoethyl)-N-methylaminophenyl, 4-N-(2'-cyanoethyl)-N-butylaminophenyl, 4-N-benzyl-N-ethylaminophenyl, 4-N-(2'-chloroethyl)-N-ethylaminophenyl or 9-ethylcarbazol-3-yl.

4. The pyridine compound as claimed in claim 2, wherein $X^1$ is 4-N,N-dimethylaminophenyl, 4-N-(2'-cyanoethyl)-N-methylaminophenyl, 4-N-(2'-cyanoethyl)-N-butylaminophenyl, 4-N-benzyl-N-ethylaminophenyl, 4-N-(2'-chloroethyl)-N-ethylaminophenyl or 9-ethylcarbazol-3-yl.

5. The pyridine compound as claimed in claim 1, wherein $X^1$ is 4-N-benzyl-N-ethylaminophenyl, 4-N-(2'-cyanoethyl)-N-butylaminophenyl, 4-N-(2'-cyanoethyl)-N-methylaminophenyl or 4-N,N-dimethylaminophenyl.

6. The pyridine compound as claimed in claim 2, wherein $X^1$ is 4-N-benzyl-N-ethylaminophenyl, 4-N-(2'-cyanoethyl)-N-butylaminophenyl, 4-N-(2'-cyanoethyl)-N-methylaminophenyl or 4-N,N-dimethylaminophenyl.

7. The pyridine compound as claimed in claim 1, wherein $X^1$ is 4-N,N-dimethylaminophenyl.

8. The pyridine compound as claimed in claim 2, wherein $X^1$ is 4-N,N-dimethylaminophenyl.

9. The pyridine compound of the formula

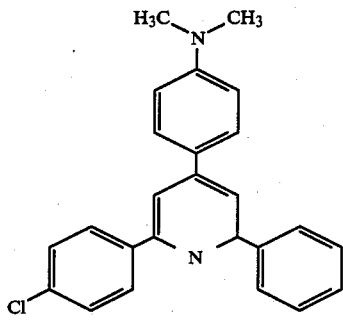

* * * * *